United States Patent
Roberts et al.

(10) Patent No.: US 10,899,606 B2
(45) Date of Patent: Jan. 26, 2021

(54) MICRONEEDLES

(71) Applicant: SPTS Technologies Limited, Newport (GB)

(72) Inventors: Kerry Roberts, Rhondda Cynon Taf (GB); Huma Ashraf, Newport (GB); Pey Fen Eng, Swansea (GB)

(73) Assignee: SPTS Technologies Limited, Newport (GB)

( * ) Notice: Subject to any disclaimer, the term of this patent is extended or adjusted under 35 U.S.C. 154(b) by 0 days.

(21) Appl. No.: 16/010,395

(22) Filed: Jun. 15, 2018

(65) Prior Publication Data
US 2018/0362334 A1 Dec. 20, 2018

(30) Foreign Application Priority Data
Jun. 16, 2017 (GB) .................................... 1709668.6

(51) Int. Cl.
*C03C 15/00* (2006.01)
*B81C 1/00* (2006.01)
(Continued)

(52) U.S. Cl.
CPC ........ *B81C 1/00111* (2013.01); *A61K 9/0021* (2013.01); *A61M 37/0015* (2013.01);
(Continued)

(58) Field of Classification Search
CPC . B81C 1/00111; B81C 1/00531; B81B 1/008; H01L 21/30655; H01L 21/32137
(Continued)

(56) References Cited

U.S. PATENT DOCUMENTS

| | | | |
|---|---|---|---|
| 6,334,856 B1 * | 1/2002 | Allen | A61B 5/14514 128/898 |
| 2008/0009763 A1 * | 1/2008 | Chiou | A61B 5/0408 600/373 |

(Continued)

FOREIGN PATENT DOCUMENTS

| | | |
|---|---|---|
| CN | 101244303 | 9/2010 |
| EP | 2036586 B1 | 9/2015 |

(Continued)

OTHER PUBLICATIONS

R. Li et al., "Continuous deep reactive ion etching of tapered via holes for three-dimensional integration," J. Micromech. Microeng. 18 (2008) 125023 (8pp).

(Continued)

*Primary Examiner* — Binh X Tran
(74) *Attorney, Agent, or Firm* — Hodgson Russ LLP

(57) ABSTRACT

A method is for manufacturing a plurality of silicon microneedles which have a bevelled tip. The method includes providing a silicon substrate having a front face and a rear face, forming a first mask arrangement on the front face of the substrate, the first mask arrangement defining one or more gaps, and performing a $SF_6$ based plasma etch of the front face through the gaps in the first mask arrangement to provide one or more etch features having a sloping face. The $SF_6$ based plasma etch undercuts the first mask arrangement with an undercut that is at least 10% of the depth of a corresponding etch feature. The method further includes forming a second mask arrangement on the etch features to define locations of the microneedles, in which the second mask arrangement is located entirely on sloping faces of the etch features, and performing a DRIE (deep reactive ion etch) anisotropic plasma etch of the etched front face of the substrate to form a plurality of microneedles which have a (Continued)

bevelled tip, where the sloping faces of the etch features at least in part give rise to the bevelled tips of the microneedles.

23 Claims, 10 Drawing Sheets

(51) Int. Cl.
H01L 21/3065 (2006.01)
A61M 37/00 (2006.01)
A61K 9/00 (2006.01)
B81B 1/00 (2006.01)

(52) U.S. Cl.
CPC . *H01L 21/30655* (2013.01); *A61M 2037/003* (2013.01); *A61M 2037/0023* (2013.01); *A61M 2037/0053* (2013.01); *B81B 1/008* (2013.01); *B81B 2201/055* (2013.01); *B81C 1/00531* (2013.01)

(58) Field of Classification Search
USPC ........................................ 216/51, 66, 74, 79
See application file for complete search history.

(56) References Cited

U.S. PATENT DOCUMENTS

| | | | | |
|---|---|---|---|---|
| 2009/0131887 | A1* | 5/2009 | Shiomitsu | A61M 37/0015 604/272 |
| 2009/0292254 | A1 | 11/2009 | Tomono | |
| 2010/0006536 | A1* | 1/2010 | Kalvesten | A61M 37/0015 216/11 |
| 2010/0280458 | A1* | 11/2010 | Cachemaille | A61M 37/0015 604/173 |
| 2011/0223542 | A1* | 9/2011 | Kendall | A61M 37/0015 430/320 |
| 2012/0058506 | A1* | 3/2012 | Gao | A61B 5/1411 435/29 |
| 2013/0338632 | A1* | 12/2013 | Kaplan | A61B 17/205 604/506 |
| 2014/0378804 | A1* | 12/2014 | Kalvesten | H01L 21/76229 600/373 |
| 2016/0220803 | A1 | 8/2016 | Kendall et al. | |
| 2016/0264408 | A1 | 9/2016 | Lui et al. | |

FOREIGN PATENT DOCUMENTS

| | | |
|---|---|---|
| WO | WO2007070004 A2 | 6/2007 |
| WO | WO2009064164 A2 | 5/2009 |
| WO | WO2015059437 | 4/2015 |

OTHER PUBLICATIONS

O. Guy et al., "Manufacture of silicon microneedles for drug & vaccine delivery," UK Research and Innovation, Swansea University, School of Engineering.

J. Ji et al., "Microfabricated Hollow Microneedle Array Using ICP Etcher," Journal of Physics: Conference Series 34 (2006), pp. 1132-1136.

H. Ngo et al., "Plasma Etching of Tapered Features in Silicon for MEMS and Wafer Level Packaging Applications " 2006 Journal of Physics: Conference Series 34 271.

P.F. Eng et al., "Silicon Microneedles for Drug Delivery and Blood Sampling Applications," Conference Paper, May 2012.

H. Gardeniers et al., "Silicon Micromachined Hollow Microneedles for Transdermal Liquid Transport," Journal of Microelectromechanical Systems, vol. 12, No. 6, Dec. 2003, pp. 855-862.

* cited by examiner

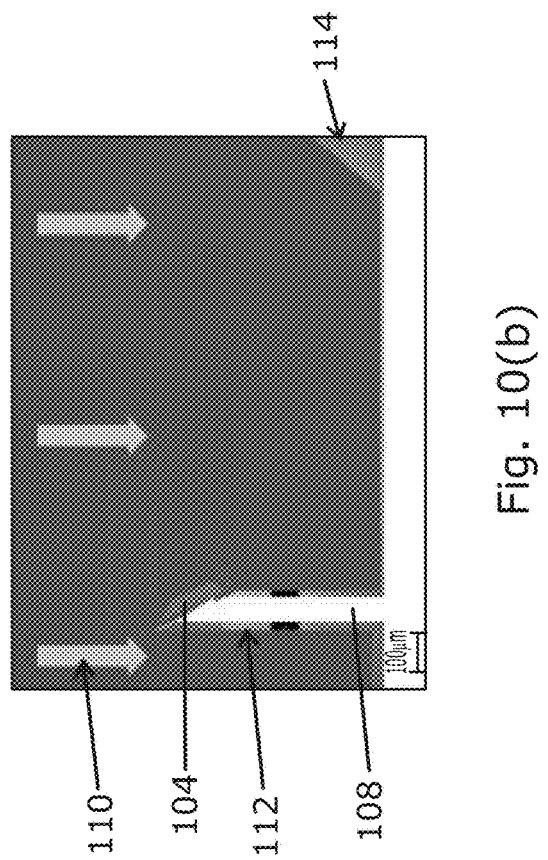
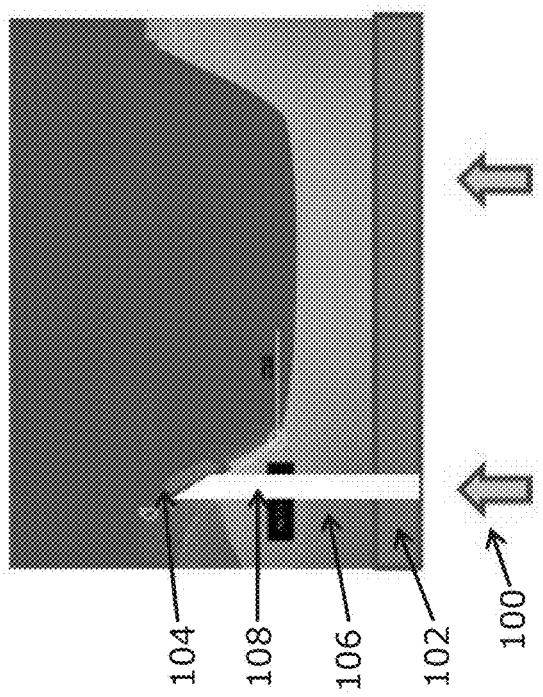
Fig. 10(a)
Fig. 10(b)

MICRONEEDLES

BACKGROUND

This invention relates to a method of manufacturing a plurality of microneedles.

It is well known to fabricate an array of microneedles as an alternative to traditional syringes and hypodermic needles for delivering drugs into patients. Microneedles are substantially smaller than traditional hypodermic needles, being fabricated on the micro scale. Microneedles have been fabricated using various methods and from various materials such as metals, silicon, silicon dioxide, polymeric materials, and glass. The mechanism of drug delivery is not based on diffusion as it is in other transdermal drug delivery products. Instead, the mechanism of drug delivery is based on a temporary mechanical disruption of the skin and the placement of the drug within the epidermis. In this way, the drug can more readily reach its site of action. The drugs may be encapsulated within the microneedles, which are then inserted into the skin and thereafter release the drug. Thousands of microneedles can be fabricated in a single process, and this can lead to high accuracy, good reproducibility, and moderate fabrication costs. Microneedles are also capable of accurate dosing, local delivery, and enhancing biological drug stability through the storage of the drugs in a micro volume that can be precisely controlled. Microneedles can also enable complex drug release patterns to be achieved. Microneedles with a length of a few hundred microns only penetrate into the superficial layers of the skin where the density of nerve receptors is low. As a consequence, the insertion of microneedles into skin is perceived as painless. Skin penetration depth requirements typically vary from ~300 microns to 500 microns depending on patient age, injection site, and application.

Microneedles fabricated from silicon constitute a promising area of development. However, process techniques for fabricating wafer-scale silicon based hollow microneedles by plasma etch process techniques have to date been prone to mechanical failure. Additionally, microneedles of this type have limited flexibility in terms of length and pitch variation, and also do not penetrate the skin reliably. It would be desirable to produce microneedles of this type which are bevelled. Bevelled microneedles would allow the needle to easily penetrate the skin and also create minimum skin trauma. However, it has not previously been possible to produce bevelled silicon microneedles using plasma etch techniques. It is known to create a bevelled tip microneedle with a wet etch using potassium hydroxide (Gardeniers et al, Journal of Microelectromechanical Systems, Vol. 12, No. 6, 2003 and US2016/0264408). However, the bevel angle created using wet etch techniques is fixed at 57.4° due to the crystallographic nature of the etch. This fixed bevel angle is a serious limitation, because it restricts flexibility to create longer needle lengths, higher bevel angles, and shorter pitches. Variations in these parameters may only be achieved with substantial changes to the overall microneedle design. A further limitation is the long processing time associated with the wet etch technique.

Known techniques to achieve sloped profiles in silicon by plasma etching typically restrict undercut and/or tailor the selectivity to masking material such that mask erosion defines the wall angle. These techniques result in very low etch rates and suffer from poor base roughness quality, or have associated etch depths which are severely restricted by mask thickness available. For etch depths of greater than 300 microns (which are typically required for microneedle fabrication), a mask having a thickness of greater than 100 microns would be required. This would be totally impractical and possibly explains why there is currently no viable plasma etch alternative to the wet etch technique described above to form bevelled microneedles.

SUMMARY

The present inventors have realised that what is needed is a method of manufacture that can form silicon microneedles having a controllable bevel angle which is user selectable and independent of the crystallographic orientation of the substrate. A related requirement is for silicon microneedles that are reliably capable of withstanding the insertion forces that are typical encountered when entering skin without damage.

The present invention, and at least some of its embodiments, addresses these needs and requirements.

According to the invention there is provided a method of manufacturing a plurality of silicon microneedles which have a bevelled tip, the method comprising the steps of:

providing a silicon substrate having a front face and a rear face;

forming a first mask arrangement on the front face of the substrate, the first mask arrangement defining one or more gaps;

performing a $SF_6$ based plasma etch of the first face through the gaps in the first mask arrangement to provide one or more etch features having a sloping face, wherein the $SF_6$ based plasma etch undercuts the first mask arrangement with an undercut that is at least 10% of the depth of a corresponding etch feature;

forming a second mask arrangement on the etch features to define locations of the microneedles, in which the second mask arrangement is located entirely on sloping faces of the etch features; and performing a DRIE (deep reactive ion etch) anisotropic plasma etch of the etched front face of the substrate to form a plurality of microneedles which have a bevelled tip, wherein the sloping faces of the etch features at least in part give rise to the bevelled tips of the microneedles.

In this way, the needs and requirements described above may be satisfied. The present invention can enable arrays of microneedles to be manufactured with improved design flexibility and with better control over the characteristics of the array. For example, shallow bevel angles are generally more suited to applications in which drugs or cells are injected to deeper layers of epidermis. Steeper bevel angles can give rise to arrays of microneedles having a reduced pitch. A further advantage is that reductions in processing times can be achieved over techniques that use a wet etch. A further advantage still is that the present invention produces microneedles having advantageous tip shapes. In particular, a tip shape may be produced having an 'asymmetrical' bevel shape in which the tip has a sharp point which is in direct connection with an upstanding sidewall of the microneedle. Microneedles of this type have excellent penetration properties.

The microneedles are generally less than 3000 microns in length and may be less than 1000 microns in length. The microneedles are generally greater than 100 microns in length. Typically, the microneedles have a length of ~300-800 micron.

The $SF_6$ based plasma etch may be formed in a gaseous mixture comprising $SF_6$ and a sidewall passivation precursor. The sidewall passivation precursor may be at least one of $C_4F_8$ and $CHF_3$. The gaseous mixture may consist essentially of $SF_6$, $CHF_3$ and $C_4F_8$.

The gaseous mixture may further comprise $O_2$. The gaseous mixture may consist essentially of $SF_6$, $O_2$ and $C_4F_8$.

The $SF_6$ based plasma etch may be formed in a gaseous mixture comprising $SF_6$ and an inert diluent. The inert diluent may be a Noble gas such as Ar. Other inert diluents, such as nitrogen, might be contemplated. The gaseous mixture may consist essentially of $SF_6$, $O_2$, $C_4F_8$ and Ar.

The DRIE plasma etch of the etched front face may be an anisotropic cyclical etch and deposition process. A cyclical etch and deposition process of the type commonly known as the 'Bosch process' may be used. Exemplary references are U.S. Pat. No. 5,501,893, U.S. Pat. No. 7,648,611 and U.S. Pat. No. 8,133,349, the entire contents of which are herein incorporated by reference.

The first mask arrangement may be an oxide mask. The oxide mask may be a thermal oxide mask.

The second mask arrangement may comprise a plurality of hard masks. The hard masks may be oxide masks.

The second mask arrangement may be deposited onto the etch features by PE-CVD (plasma enhanced chemical vapour deposition). This is a suitable way of depositing hard masks, such as oxide hard masks. Alternatively, the second mask arrangement may comprise a photoresist or a plurality of metal masks.

In general, front side plasma etching of the second mask using the DRIE anisotropic plasma etch process takes place to achieve a front side cavity etch.

The method may further comprise a step of performing a DRIE plasma etch of the rear face to form a plurality of channels in the silicon substrate which are positioned so that, after the plurality of microneedles are formed, the channels act as bore passages extending through the microneedles. The DRIE plasma etch of the rear face may be a cyclical etch and deposition process. A cyclical etch and deposition process of the type commonly known as the 'Bosch process' may be used. The step of performing a DRIE plasma etch of the rear face may be performed prior to the step of performing a DRIE plasma etch of the etched front face. Alternatively, the step of performing a DRIE plasma etch of the rear face may be performed after the step of performing a DRIE plasma etch of the etched front face. In other words, the steps of performing a DRIE plasma etch of the rear face and of performing a DRIE plasma etch of the etched front face are interchangeable.

A third mask arrangement may be formed on the back face prior to the step of performing a DRIE plasma etch of the back face. Typically, the third mask arrangement is aligned with corresponding features on the second mask. In this way, the third mask arrangement may define a plurality of gaps which correspond to the locations of the plurality of channels in the silicon substrate. The third mask arrangement may comprise a hard mask, which may be an oxide mask. The third mask arrangement may be deposited onto the back face by PE-CVD. This is a suitable way of depositing a hard mask, such as an oxide mask. Alternatively, the third mask arrangement may comprise a photoresist or a metal mask.

Typically, the $SF_6$ based plasma etch of the first face through the gaps in the first mask arrangement provides one or more etch features having a pair of opposed sloping faces. The second mask arrangement may be formed only on one of the pair of opposed sloping faces of each etch feature.

The bevelled tips of the microneedles may be formed as single bevel structures.

Alternatively, the bevelled tips of the microneedles may be formed as double bevel structures. Double bevel structures can provide enhanced skin penetration performance. Double bevel structures may be formed by controlling etch conditions during the step of performing a $SF_6$ based plasma etch of the front face.

Alternatively still, the step of performing a $SF_6$ based plasma etch of the front face may produce single bevel structures. Double bevel structures may then be produced during the step of performing a DRIE plasma etch of the etched front face. The second mask arrangement may comprise oxide masks having a thickness in the range 3 to 5 microns. This is an effective way of producing a double bevel structure.

The DRIE plasma etch of the etched front face may form one or more ridge structures which are spaced apart from the microneedles. The ridge structures can provide a more robust structure which is better able to withstand shear forces. Each microneedle may be spaced 100 to 1000 microns, preferably 100 to 600 microns, apart from its nearest ridge structure. A plurality of interconnected ridge structures may be formed to provide a plurality of microneedle surrounding fence structures each of which surround and are spaced apart from a microneedle.

The ridge structures may be formed in the following way:
the $SF_6$ based plasma etch may etch through a gap in the first mask arrangement to provide one or more etch features which have a pair of opposed sloping faces, and
the DRIE plasma etch of the etched front face may be performed so that one of the pair of opposed sloping faces at least in part gives rise to the bevelled tip of a microneedle and the other of the pair of opposed sloping faces at least in part gives rise to a ridge which is spaced apart from the microneedle.

The bevelled tips of the microneedles may have a bevel angle in the range 50 to 85°.

The bevelled tips of the microneedles may have a bevel angle of at least 60°. The bevel angle may be at least 70°. The bevel angle may be 85° or less.

Generally, the bevelled tip is pointed. The bevelled tip may be diamond shaped.

The gaps defined by the first mask arrangement may each have a width. The etch features may each have a base width. The base width of each etch feature may be substantially equal to the width of its corresponding gap in the first mask arrangement. Preferably, the base width of each etch feature is within 10% of the width of its corresponding gap in the first mask arrangement.

The microneedles of the invention can be used in a wide range of applications. The microneedles may be hollow, pocketed or solid. The microneedles may deliver any desired beneficial substance, such as a drug, cells or other therapeutic substance, when inserted into the skin. In principle, the microneedles might instead not be used to deliver a beneficial substance.

Whilst the invention is described above, it extends to any inventive combination of the features set out above or in the following description, drawings or claims.

BRIEF DESCRIPTION OF THE DRAWINGS

Embodiments of methods in accordance with the invention will now be described with reference to the accompanying drawings, in which:—

FIG. 10(a) shows annotated SEM micrographs of a bore channel etched in the bulk silicon substrate and FIG. 10(b) shows the same of a microneedle formed at the end of a front face etch of the bulk silicon substrate;

DETAILED DESCRIPTION OF EMBODIMENTS

Figure 1:
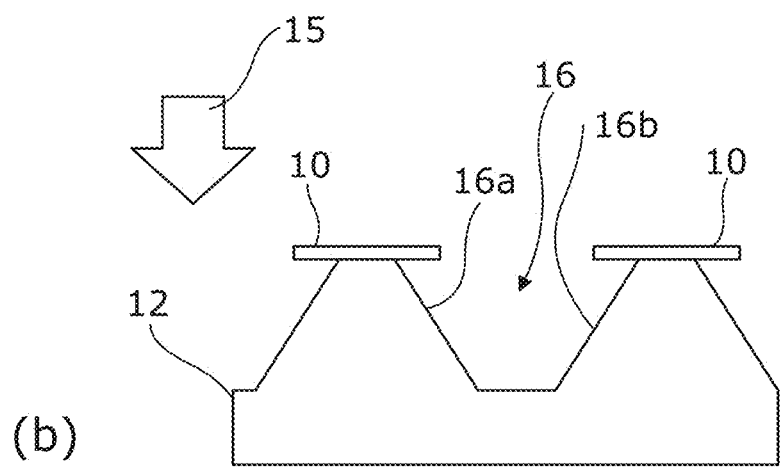
FIG. 1 shows (a) a plan view of a silicon substrate with a first mask and (b) a cross sectional view of the silicon substrate at the end of a $SF_6$ based etch.
Figure 1:
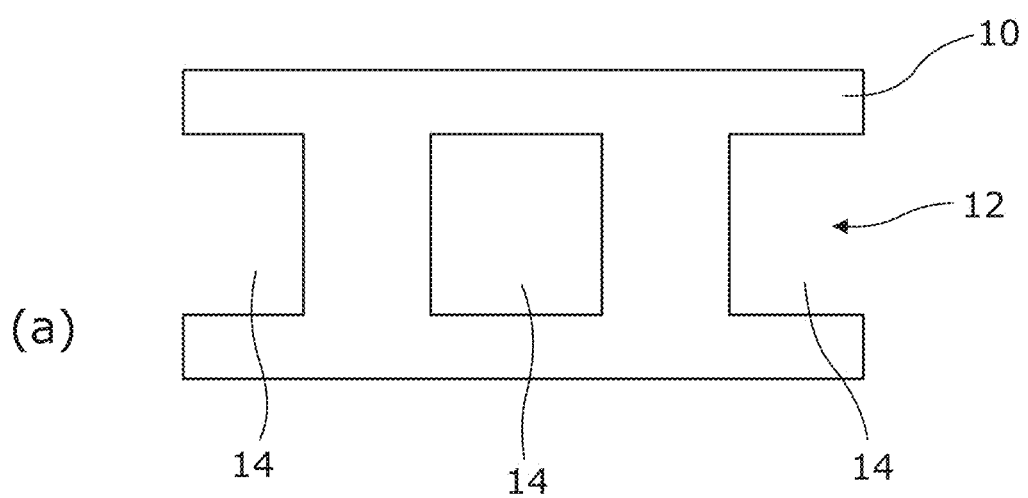
Figure 2:
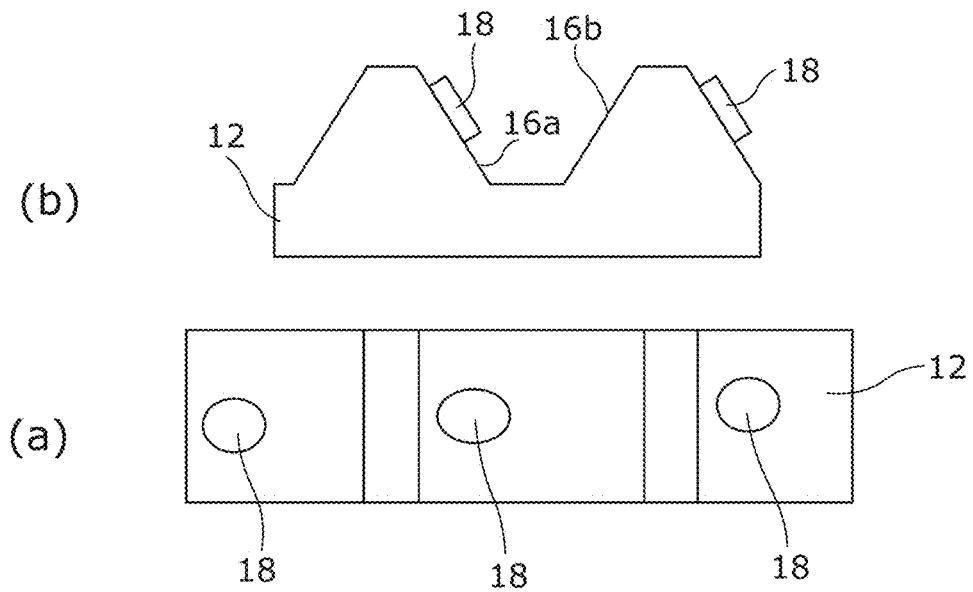
FIG. 2 shows (a) a plan and (b) a cross sectional views of the silicon substrate with a second mask arrangement on the front face.
Figure 3:
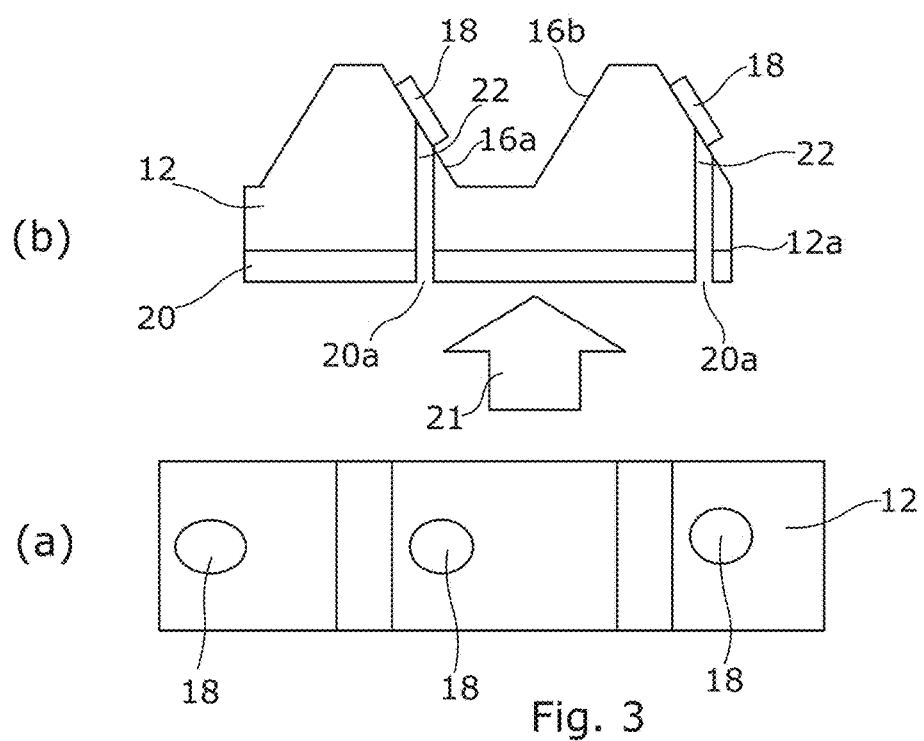
FIG. 3 shows (a) a plan and (b) a cross sectional views of the silicon substrate with a third mask on the rear face at the end of a backside etch.
Figure 4:
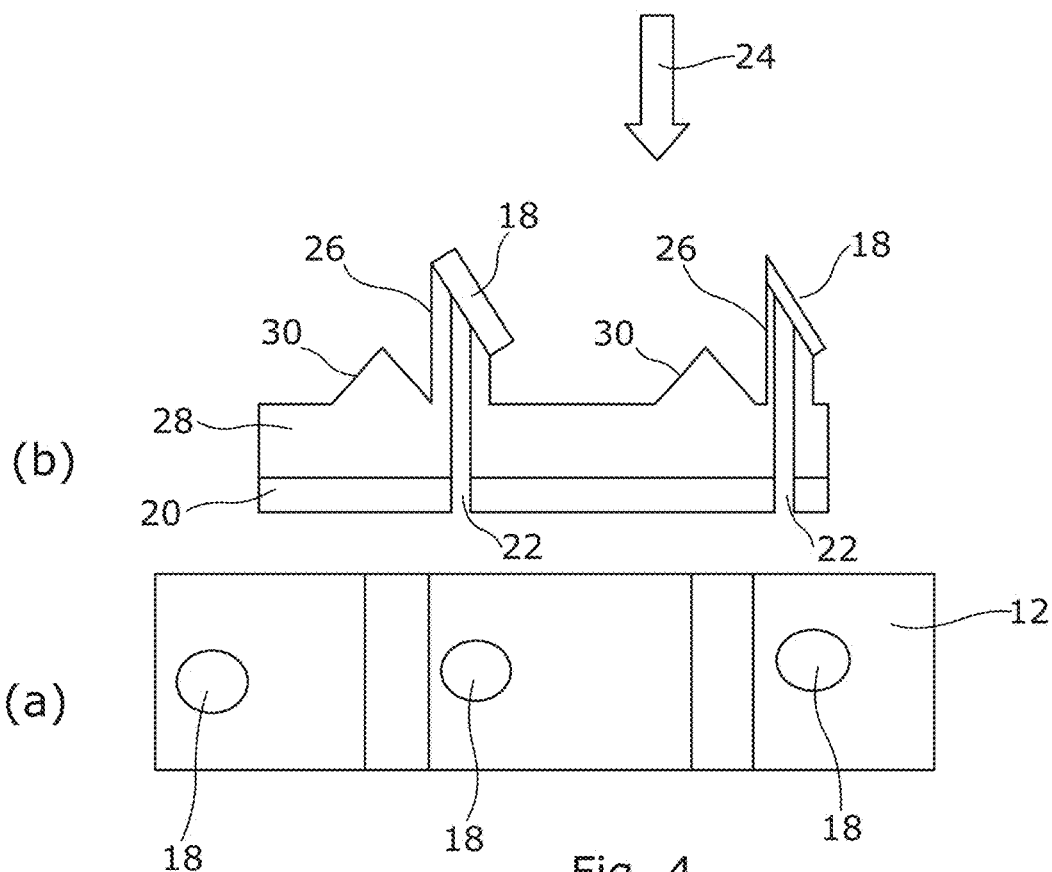
FIG. 4 shows (a) a plan and (b) a cross sectional views of microneedles formed at the end of a front face etch.
Figure 5:
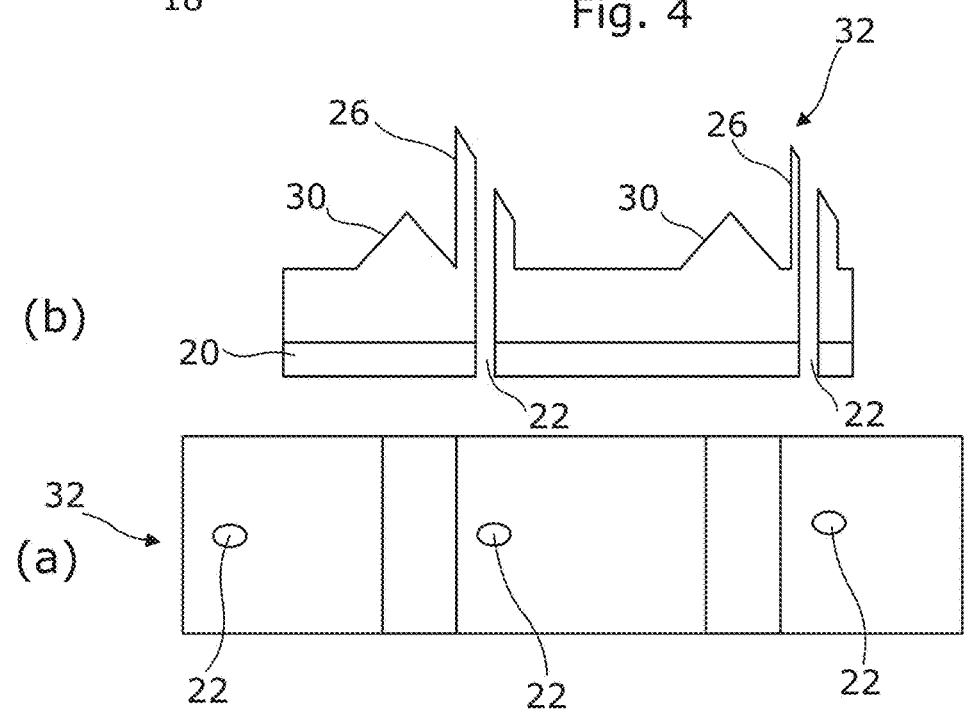
FIG. 5 shows (a) a plan and (b) a cross sectional views of the microneedles after removal of the second mask arrangement.

FIGS. 1 to 5 show steps in a representative but non-limiting method of the invention. FIG. 1A shows a portion of a first mask 10 which is formed on a silicon substrate 12. The first mask 10 defines a plurality of apertures 14 to reveal exposed portions of a front face of the silicon substrate 12. The first mask 10 as shown in FIG. 1A consists of a row of apertures 14. As will be explained below, this gives rise to a row of microneedles. In practice, it is common to use a more extended first mask which defines rows and columns of apertures 14. The more complicated first masks of this type give rise to an array of microneedles having both rows and columns of microneedles. The skilled reader will appreciate that the first mask can take many different forms depending on the preferred form of the microneedles desired for any particular application.

The silicon substrate 12 having the first mask 10 is then subjected to a $SF_6$ based plasma etch 15. This is shown in FIG. 1B. The plasma etch etches through the apertures 14 in the first mask 10 to produce a plurality of etch features. FIG. 1B is a cross sectional view of the silicon substrate/first mask towards the end of the $SF_6$ based plasma etch, at which point a plurality of etch features 16 have been formed which comprise a pair of opposed sloping faces 16A, 16B. It can be seen that the $SF_6$ based plasma etch undercuts the first mask 10. The undercut is the amount of lateral etching underneath the mask. In practice, the undercut achieved is at least 10% of the depth of a corresponding etch feature 16.

The first mask 10 is removed and second masks 18 are formed on one sloping face 16A of the pairs of opposing sloping faces 16A, 16B (FIGS. 2A and B). The other sloping face 16B of a pair is not protected by a mask. A third mask 20 is formed on the rear face 12A of the silicon substrate 12. The third mask 20 is formed with a plurality of apertures 20a in the mask which are aligned with the locations of the second mask 18 on the sloping faces 16A. As shown in FIGS. 3A and B, a backside plasma etch 21 of the masked rear face 12A of the silicon substrate is then performed to form a plurality of bore channels 22 which extend from the apertures 20 through the silicon substrate 12 to reach the second masks 18. The plasma etch used to form the bore channels 22 can be any convenient etch process. It is very convenient to use a DRIE etch such as a Bosch type etch. Next, a DRIE plasma etch of the front side of the silicon substrate 12 plasma etch is performed. FIGS. 4A and B show the DRIE plasma etch 24 of the front face of the silicon substrate 12. The plasma etch 24 etches the bulk silicon around the second masks 18 to leave a plurality of bevelled microneedle structures 26 upstanding from a base layer 28. It will be apparent that the plasma etch 24 can be controlled so as to control the depth of the base layer 28 and the height of the microneedle structures 26. Advantageously, the plasma etch 24 also forms a plurality of ridge structures 30 which are spaced from the microneedle structures 26. The ridge structures are associated with the etching of portions of the front face of the silicon substrate 12 which at least include the sloping faces 16B.

The second masks 18 are then removed to produce the microneedle array 32 shown in FIGS. 5A and B. The microneedle array 32 comprises a plurality of bevelled microneedle structures 26. In the embodiment shown in FIGS. 5A and B, the microneedle structures 26 are hollow due to the presence of bore channels 20 extending therethrough. The embodiment shown in FIGS. 5A and B also comprises the plurality of ridge structures 30. In practice, it is usual for the microneedle array to be formed with a far greater number of microneedle structures. In the embodiment shown in FIGS. 5A and B, the third mask 20 on the rear face 12A remains in place. Optionally, the third mask 20 could be removed.

Figure 6B:
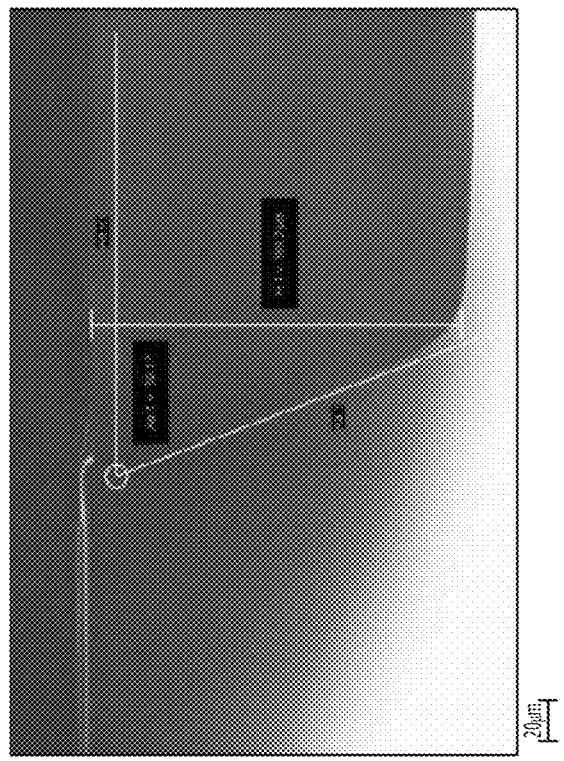
FIG. 6(a) shows SEM (scanning electron microscope) micrographs of a first etch feature and FIG. 6(b) shows the same of a second etch feature after a $SF_6$ based etch.
Figure 6A:
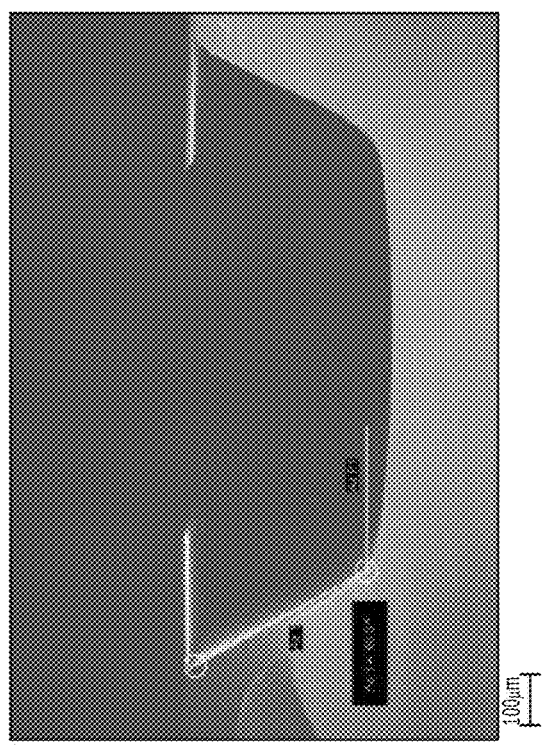

Although it is desirable to provide a dry etch process which creates sloped sidewalls in a silicon substrate to a depth of several hundred microns, in practice this has been very hard to achieve. The present invention provides a $SF_6$ based dry plasma etch which can be used to create sloped sidewalls which can be further processed to provide a plurality of bevelled microneedles. Examples of suitable $SF_6$ based gas mixtures include: $SF_6/O_2/C_4F_8$; $SF_6/O_2/C_4F_8/Ar$; $SF_6/O_2/A_r$; and $SF_6/CHF_3/C_4F_8$. Other $SF_6$ based gaseous compositions might be used. These compositions may be with or without oxygen and/or with or without an inert diluent such as argon. The relative proportion of the constituents may also be varied in order to achieve desired profiles. The $SF_6$ based plasma forms the basis of an isotropic etch. It is desirable to add a constituent such as $C_4F_8$ and/or $CHF_3$ to achieve some sidewall passivation. The sidewall passivation restricts lateral etching and helps to maintain a profile which is free from "overhang". Typically, the etch achieves a large undercut below the first mask, but the sidewalls become passivated due to ion-assisted migration or diffusion of polymeric moieties from the base of the etch feature to the sidewalls. FIGS. 6A and B show SEMs of etch features achieved using typical process conditions for the $SF_6/C_4F_8$ based first plasma etch In both instances, the first mask can be clearly seen as essentially horizontal white lines towards the top of each FIGS. 6A and B. FIG. 6A shows a gap defined by the first mask. In FIG. 6A, it can be seen that the width of the opening defined by the first mask is similar to the base width of the etch feature. This is a typical but non-limiting result. In FIG. 6a, the $SF_6$ based plasma etch has produced a substantially flat base with a pair of opposed sloping sidewalls having a 60.9° profile angle. The $SF_6$ based plasma etch has resulted in an undercut of the first mask which is greater than 200 microns. In FIG. 6B, a sloping sidewall is produced having a profile angle of 69.1° and a depth of 188 microns.

Typical process contents for the $SF_6$ based plasma etch are: platen temperature 20° C.; pressure 60 mTorr; 4 kW source RF; 10 W platen RF; 575 sccm $SF_6$ flow rate; 100 sccm $C_4F_8$ flow rate; 80 sccm $O_2$ flow rate.

A typical etch rate is in the range 10-20 microns/min, with a process time of around 20 minutes.

Figure 7:
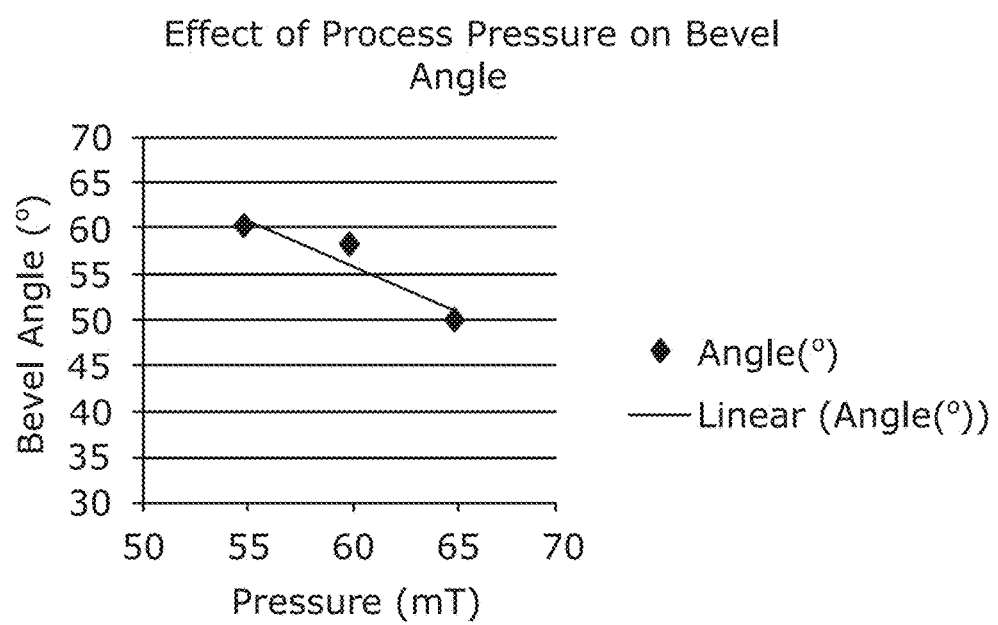
FIG. 7 shows the effect of process pressure during the $SF_6$ based etch on bevel angle.

It is possible to control the profile angle of the sloping faces by modifying the process parameters. For example, increasing the power applied to the platen can increase the profile angle. Variation of the flow of $C_4F_8$ can either increase or decrease the profile angle depending on the feature size and geometry. Additionally, the process pressure can affect the profile angle, which in turn affects the bevel angle of the eventually produced microneedles. FIG. 7 shows the variation in the bevel angle as a function of process pressure. It can be seen that lower process pressures give rise to steep bevel angles. Without wishing to be limited by any particular theory or conjecture, it is believed that increasing the process pressure and/or reducing the platen power changes the angle of distribution of the etchant species, and this directly affects the bevel angle. This, in combination with simultaneous passivation of the sidewalls, controls the overall profile. The simultaneous passivation can be of all of the sidewalls or a portion of the sidewalls. It is possible to produce microneedles having a single bevel tip or a double bevel tip by varying the process conditions of the $SF_6$ based plasma etch in this way. Alternatively, a double bevel tip can be achieved in combination with passivation steps where the lower parts of the sidewalls and base are protected from lateral etching, whilst the upper parts of the sidewalls are etched to produce shallow profile angles.

Figure 8B:
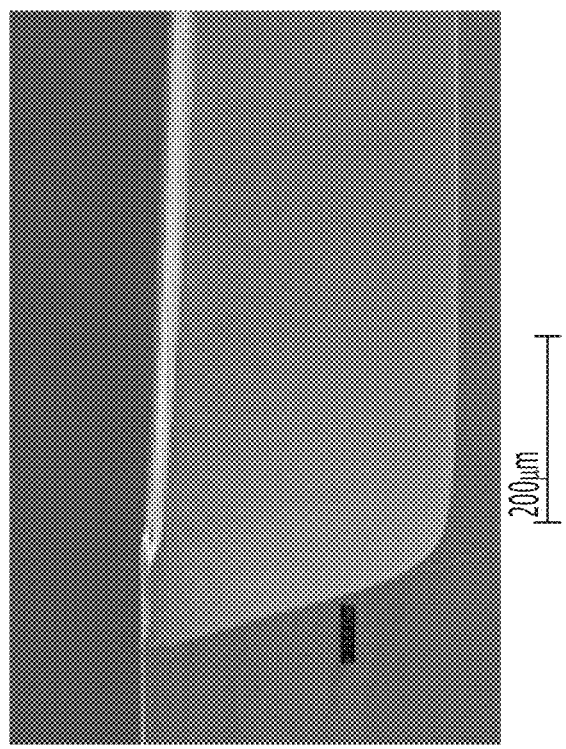
FIG. 8(a) shows SEM micrographs of a third etch feature and FIG. 8(b) shows the same of a fourth etch feature after a $SF_6$ based etch.
Figure 8A:
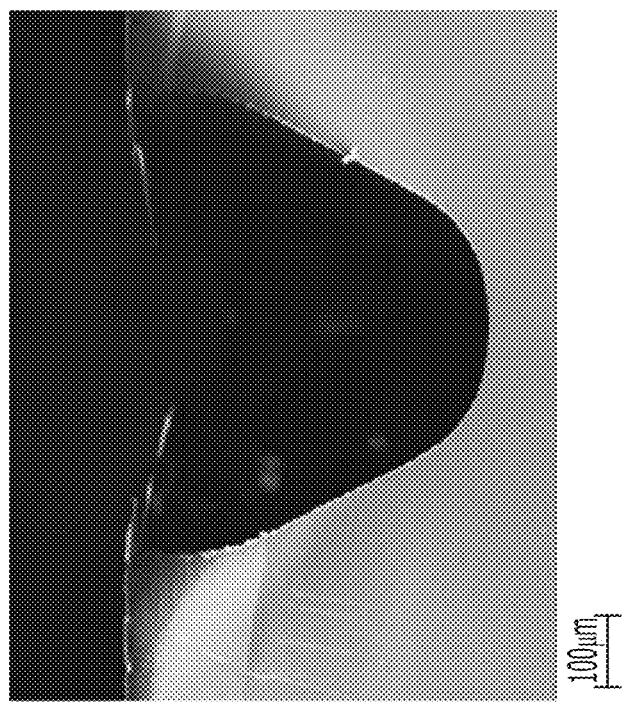
Figure 9:
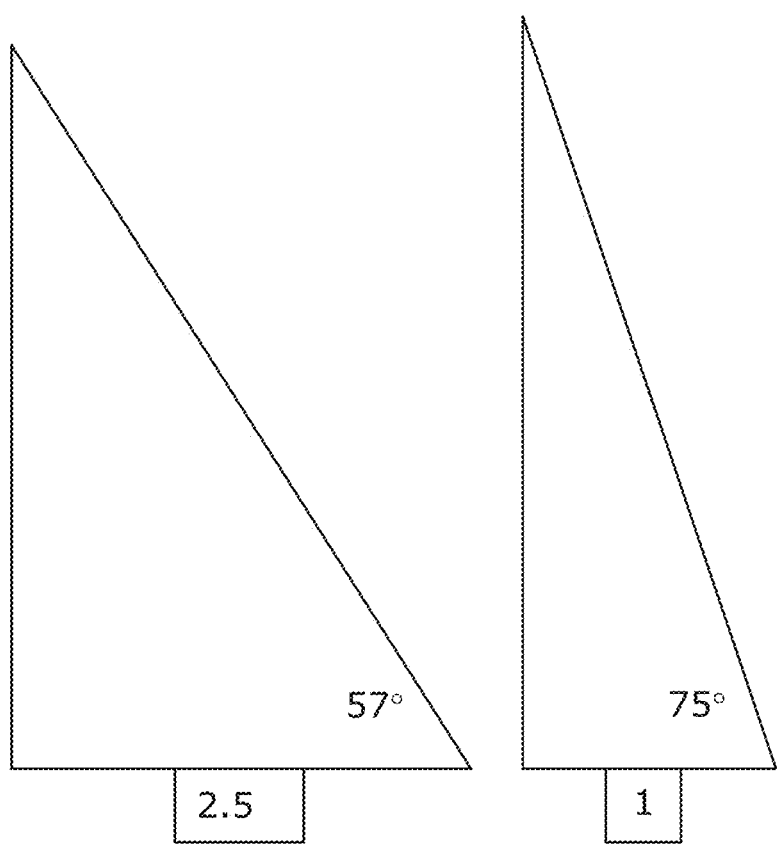
FIG. 9 shows the effect of bevel angle (57° and 75°) on microneedle width.

FIGS. 8A and B show SEMs of further bevel etch features achieved using a $SF_6/C_4F_8/O_2$ plasma etch chemistry. In FIG. 8A a "strawberry" etch profile is achieved, with the sloping sidewalls having a main profile angle of 59.4°. The depth of the etch feature is 420 microns and an etch rate of 16.8 microns/min was achieved. In FIG. 8B, a steep profile angle of 75° is achieved and the etch depth is 331 microns. It is highly advantageous that the profile angle and hence the bevel angle can be readily controlled using the dry etch method of the invention. Additionally, it is highly advantageous that the invention can provide steep profile angles and hence steep bevel angles. FIG. 9 shows the effect of changing the bevel angle from 57° to 75° on microneedle width. It can be seen that there is a 2.5× reduction in the diameter of the microneedle if the bevel angle is increased from 57° to 75° for a fixed bevel length This is a key factor in the production of high density silicon microneedle arrays. 57° corresponds to the bevel angle produced using wet etch techniques. This bevel angle is set owing to the crystallographic nature of the wet etch. Consequently, the prior art wet etch technique places a fundamental constraint on the design of the microneedle array. The present invention overcomes this limitation in the prior art. A further advantage of the dry etch method provided by the invention is that there is a substantial reduction in process time compared to a standard KOH wet etch. Typical process times for a dry etch of the invention are around 20 minutes to produce microneedles of 400 micron length. In contrast, a KOH wet etch would take about 22 hours microneedles of the same length. Additionally, the dry etch method of the invention avoids problems associated with roughness that are caused by a wet etch technique. The present invention can produce profile angles of 50°-80° and etch feature depths of 150-400 microns. However, the invention is not limited to these angles and depths.

After the first etch is completed, the first mask is removed using known means. FIGS. 10A and B are annotated SEMs depicting further stages in the production of the microneedles. FIG. 10A shows the silicon substrate 106 after exposure to the backside plasma etch 100. A second mask 104 is positioned on a sloping sidewall partially to act as an etch stop for the backside plasma etch. The third mask 104 is positioned on the rear face of the silicon substrate 104 and is patterned to expose portions of the silicon to the backside plasma etch in order to form bore channels 108. The masks 102, 104 are aligned to ensure that the etching of the bore channel 108 stops at the second mask 104. The silicon substrate 106 is placed with the third mask 102 facing the plasma 100, and the bore channel etch is completed once all of the silicon above the aperture in the third mask has been removed, resulting in a bore channel 108. FIG. 10B shows the subsequent plasma etch of the front face of the silicon substrate using a DRIE plasma etch 110. The second mask 104 protects the silicon underneath it from the plasma 110 whilst bulk silicon is removed by the plasma 110 in unmasked areas. The plasma 110 is substantially anisotropic in nature, resulting in the formation of a hollow, bevelled microneedle 112. The plasma 110 also produces a ridge 114. The ridge 114 is associated with the sloping face of the etch feature which is opposite to the sloping face which produces the microneedle 112. After the processing of the plasma 110 is completed, the second and, optionally, the third masks can be removed using known means. Typically, a PE-CVD oxide is used to form a hard second mask 104. However, alternative materials such as a photo resist or a metal mask could be used instead. The third mask 102 may also be formed from a hard mask, photo resist or metal mask. Conveniently, the second and third masks are formed form the same material. The front side plasma etch which forms the microneedles is a DRIE plasma etch. Conveniently, a typical cyclical etch and deposition process can be used with ICP HF source powers 3-6 kW, bias power 0.12-1.5 kW, process pressures 40-50 mT, cycle time 1-5 seconds and principally $SF_6$ during the etch cycle and $C_4F_8$ during the deposition cycle.

The front side plasma etch is desirably substantially anisotropic, and in fact it is possible to produce microneedles with completely vertical upstanding walls. However, it is generally preferred to provide microneedles having a re-entrant shape (wider top, narrower base) because the plasma etch processes which create re-entrant angles are typically less polymeric in nature, and hence more repeatable and robust. The backside plasma etch may be of the same type as the front face plasma etch which is used to produce the microneedles. In some embodiments, the same etch process is used for both the backside and front face etches.

Figure 11:
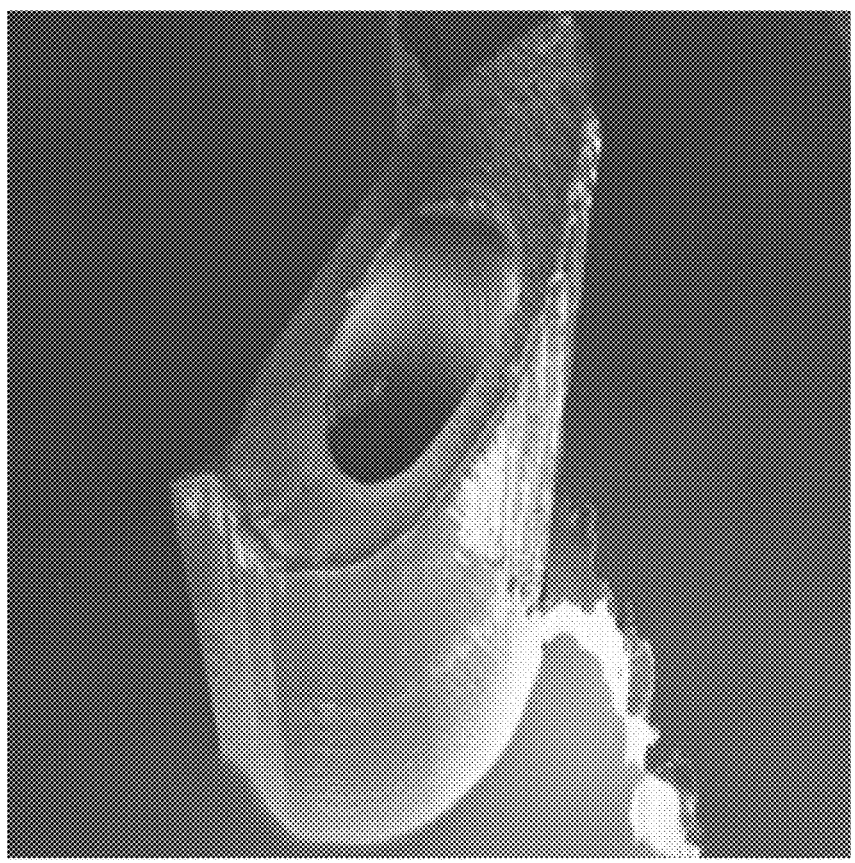
FIG. 11 is a SEM micrograph of a single bevelled microneedle.
Figure 12B:
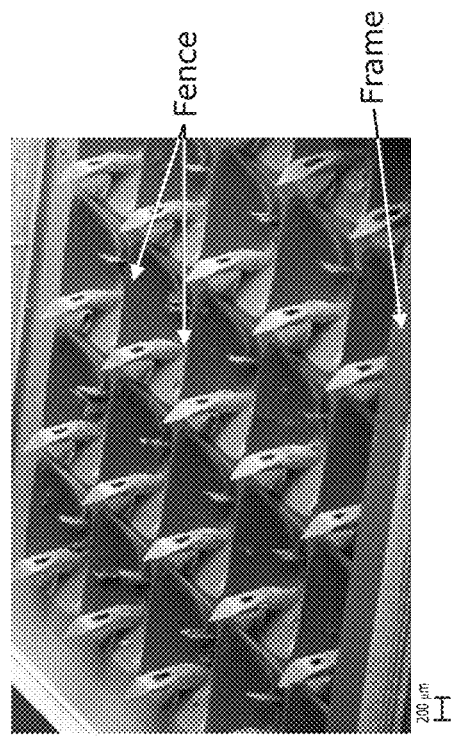
FIG. 12 (a) shows a high resolution SEM micrograph of double bevelled microneedles in front of a fence, and FIG. 12(b) a lower resolution SEM micrograph of an array of double bevelled microneedles with fence structures present.
Figure 12A:
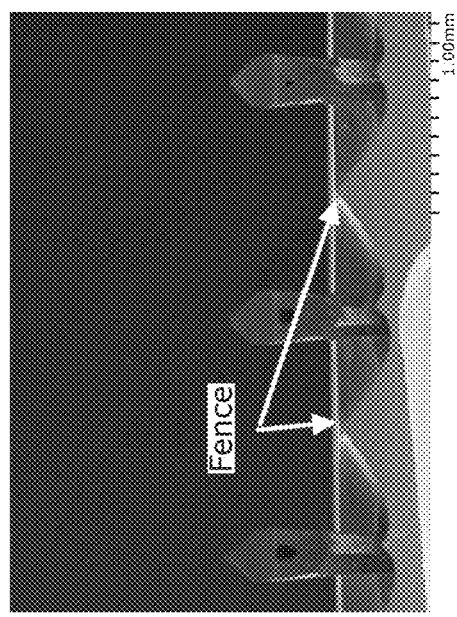

The front face plasma etch can be used to obtain single or double bevelled microneedle tips. It has been found that if a relatively thick oxide second mask having a thickness of greater than 5 microns is used, then a single bevel structure can be obtained as can be seen in FIG. 11 As noted previously, a double bevelled microneedle tip can be obtained through appropriate control of the $SF_6$ based first etch. It has been found that double bevel tips can also be obtained through control of the front face etch of the silicon substrate which produces the microneedles. Due the higher incidents of energetic ions, the etch rate of the second mask at the bottom of the bevelled structure is much higher than at the top. As a result, the portions of the second mask at the bottom of the bevelled structure experience a much higher etch rate than the portions of the mask at the top. Therefore, the portions of the second mask at the bottom of the bevel structure are consumed more quickly, leading to etching of the underlying silicon. This leads to the formation of a double bevelled structure. It has been found that the use of an oxide second mask having a thickness in the range 3-5 microns results in double bevelled structures. Second masks formed from different materials may require a different range of thicknesses used in order to produce double bevelled structures. Both single and double bevelled structures are of practical utility, and it is advantageous that the present invention can provide microneedles having either structure. Double bevelled structures have improved skin penetration yields. FIGS. 12A and B show SEM images of double bevelled microneedles in which the top bevel angle is about 60° and the bottom bevel angle is steeper at about 80°. Microneedles having bevelled tips of a diamond shape result in the most effective skin puncture. The microneedles shown in FIGS. 12A and B have the desired diamond shaped tips, and in fact microneedles with diamond shaped tips can be readily produced using the present invention.

As explained above, it is possible to form a ridge which is spaced apart from an adjacent microneedle. When an array of microneedles is produced using a first mask that comprises rows and columns of apertures, the ridges can form a plurality of fence structures which surround the microneedles. This can be seen particularly clearly in FIG. 12B. The perimeter of the silicon substrate which was masked by the first mask forms a frame structure which surrounds the array of microneedles. The ridges are typically formed at a distance of 100-200 microns from the base of the adjacent microneedles. However, smaller or greater distances can be utilised, primarily through appropriate design of the first mask but also through control of the etch processes. The presence of the ridges/frame structures is advantageous for a number of reasons. The likelihood of breakage of the microneedles (which is primarily caused by shear forces during injection of the microneedles into the skin) is reduced. The ridge/fence structures also allow stretching and bunching of the skin area local to the microneedles to give better skin penetration. Another advantage is that the ridge/fence structures can be used to define the microneedle penetration depth. The positioning of the microneedle shaft alongside the ridge/fence structures defines a needle penetration depth which is related to the difference between the microneedle height and the ridge height. This enables target drug delivery depth to be achieved.

Many variations to the method as described above would readily suggest themselves to the skilled reader. For example, it is not essential that hollow microneedles are produced. Instead, solid microneedles might be manufactured by omitting the backside etch step. Alternatively, pocketed microneedles might be produced having pockets or cavities formed either in the tip or in the microneedle body. Although the microneedles exemplified above have a cylindrical body shape, it is possible to instead produce microneedles having non-cylindrical body shapes of various forms.

What is claimed is:

1. A method of manufacturing a plurality of silicon microneedles which have a bevelled tip, the method comprising the steps of:

providing a silicon substrate having a front face and a rear face;

forming a first mask arrangement on the front face of the substrate, the first mask arrangement defining one or more gaps;

performing a $SF_6$ based plasma etch of the front face through the gaps in the first mask arrangement to provide one or more etch features having a sloping face, wherein the $SF_6$ based plasma etch undercuts the first mask arrangement with an undercut that is at least 10% of the depth of a corresponding etch feature;

forming a second mask arrangement on the etch features to define locations of the microneedles, in which the second mask arrangement is located entirely on sloping faces of the etch features; and performing a DRIE (deep reactive ion etch) anisotropic plasma etch of the etched front face of the substrate to form a plurality of microneedles which have a bevelled tip, wherein the sloping faces of the etch features at least in part give rise to the bevelled tips of the microneedles.

2. A method according to claim 1 in which the DRIE plasma etch of the etched front face is an anisotropic cyclical etch and deposition process.

3. A method according to claim 1 in which the first mask arrangement is an oxide mask.

4. A method according to claim 1 in which the second mask arrangement is deposited onto the etch features by PE-CVD (plasma enhanced chemical vapour deposition).

5. A method according to claim 1 in which the bevelled tips of the microneedles are formed as single bevel structures.

6. A method according to claim 1 in which the bevelled tips of the microneedles have a bevel angle of at least 60°.

7. A method according to claim 1 in which: the gaps defined by the first mask arrangement each have a width; the etch features each have a base width; and the base width of each etch feature is substantially equal to the width of its corresponding gap in the first mask arrangement.

8. A method according to claim 1 in which the $SF_6$ based plasma etch is formed in a gaseous mixture comprising $SF_6$ and an inert diluent.

9. A method according to claim 8 in which the gaseous mixture consists essentially of $SF_6$, $O_2$, $C_4F_8$ and Ar.

10. A method according to claim 1 further comprising the step of performing a DRIE plasma etch of the rear face to form plurality of channels in the silicon substrate which are positioned so that, after the plurality of microneedles are formed, the channels act as bore passages extending through the microneedles.

11. A method according to claim 10 in which the step of performing a DRIE plasma etch of the rear face is performed prior to the step of performing a DRIE plasma etch of the etched front face.

12. A method according to claim 1 in which the DRIE plasma etch of the etched front face forms one or more ridge structures which are spaced apart from the microneedles.

13. A method according to claim 12 in which a plurality of interconnected ridge structures are formed to provide a plurality of microneedle surrounding fence structures each of which surround and are spaced apart from a microneedle.

14. A method according to claim 12 in which:

the $SF_6$ based plasma etch etches through a gap in the first mask arrangement to provide one or more etch features which have a pair of opposed sloping faces, and the DRIE plasma etch of the etched front face is performed so that one of the pair of opposed sloping faces at least in part gives rise to the bevelled tip of a microneedle and the other of the pair of opposed sloping faces at least in part gives rise to a ridge which is spaced apart from the microneedle.

15. A method according to claim 1 in which the bevelled tips of the microneedles are formed as double bevel structures.

16. A method according to claim 15 in which the double bevel structures are formed by controlling etch conditions during the step of performing a $SF_6$ based plasma etch of the front face.

17. A method according to claim 15 in which the step of performing a $SF_6$ based plasma etch of the front face produces single bevel structures, and the double bevel structures are produced during the step of performing a DRIE plasma etch of the etched front face.

18. A method according to claim 17 in which the second mask arrangement comprises oxide masks having a thickness in the range 3 to 5 microns.

19. A method according to claim 1 in which the $SF_6$ based plasma etch is formed in a gaseous mixture comprising $SF_6$ and a sidewall passivation precursor.

20. A method according to claim 19 in which the sidewall passivation precursor is at least one of $C_4F_8$ and $CHF_3$.

21. A method according to claim 20 in which the gaseous mixture consists essentially of $SF_6$, $CHF_3$ and $C_4F_8$.

22. A method according to claim 19 in which the gaseous mixture further comprises $O_2$.

23. A method according to claim 22 in which the gaseous mixture consists essentially of $SF_6$, $O_2$ and $C_4F_8$.

* * * * *